(12) United States Patent
Akbarian et al.

(10) Patent No.: US 11,806,026 B2
(45) Date of Patent: Nov. 7, 2023

(54) SHAVER WITH BLOOD VESSEL AND NERVE MONITORING FEATURES

(71) Applicant: Acclarent, Inc., Irvine, CA (US)

(72) Inventors: Fatemeh Akbarian, Rancho Palos Verdes, CA (US); Jetmir Palushi, Irvine, CA (US); Ehsan Shameli, Irvine, CA (US)

(73) Assignee: Acclarent, Inc., Irvine, CA (US)

( * ) Notice: Subject to any disclaimer, the term of this patent is extended or adjusted under 35 U.S.C. 154(b) by 169 days.

(21) Appl. No.: 17/384,854

(22) Filed: Jul. 26, 2021

(65) Prior Publication Data

US 2022/0015777 A1 Jan. 20, 2022

Related U.S. Application Data (62) Division of application No. 15/984,473, filed on May 21, 2018, now Pat. No. 11,103,256.

(51) Int. Cl.
*A61B 17/16* (2006.01)
*A61B 17/00* (2006.01)
*A61B 5/24* (2021.01)

(52) U.S. Cl.
CPC ...... *A61B 17/1659* (2013.01); *A61B 17/1615* (2013.01); *A61B 17/1688* (2013.01);
(Continued)

(58) Field of Classification Search
CPC ........... A61B 2017/32002; A61B 2017/32004; A61B 2017/320028; A61B 2017/320032;
(Continued)

(56) References Cited

U.S. PATENT DOCUMENTS 3,937,222 A * 2/1976 Banko ................. A61F 9/00763
606/107
5,913,867 A 6/1999 Dion
(Continued)

FOREIGN PATENT DOCUMENTS

EP 0338965 A1 10/1989
WO WO 2005 091978 A2 10/2005
WO WO 2013/071299 A2 5/2013

OTHER PUBLICATIONS

International Search Report and Written Opinion dated Jul. 17, 2019, for Application No. PCT/IB2019/053633, 14 pages.
(Continued)

*Primary Examiner* — Matthew J Lawson
(74) *Attorney, Agent, or Firm* — Frost Brown Todd LLP (57) ABSTRACT

A surgical instrument for cutting a first tissue and detecting a second tissue includes a shaft, a cutting member, and a tissue monitor system. The shaft extends along a longitudinal axis and includes a shaft lumen and a shaft opening. The cutting member is disposed within the shaft lumen and configured to cyclically move from a first position to a second position relative to the shaft. The cutting member is further configured to cut a tissue portion of the first tissue for removal therefrom. The tissue monitor system is associated with at least one of the shaft or the cutting member configured to detect the second tissue distinct from the first tissue for selectively cutting and removing the first tissue relative to the second tissue.

20 Claims, 4 Drawing Sheets

(52) U.S. Cl.
CPC ....... *A61B 5/24* (2021.01); *A61B 2017/00022* (2013.01); *A61B 2017/00061* (2013.01); *A61B 2017/00106* (2013.01); *A61B 2017/00115* (2013.01); *A61B 2017/00398* (2013.01); *A61B 2217/005* (2013.01)

(58) Field of Classification Search
CPC ............ A61B 17/1659; A61B 17/1624; A61B 17/1688
See application file for complete search history.

(56) References Cited

U.S. PATENT DOCUMENTS

| | | |
|---|---|---|
| 7,720,521 B2 | 5/2010 | Chang et al. |
| 8,007,506 B2 | 8/2011 | To et al. |
| 8,123,722 B2 | 2/2012 | Chang et al. |
| 8,190,389 B2 | 5/2012 | Kim et al. |
| 8,320,711 B2 | 11/2012 | Altmann et al. |
| 8,568,418 B2 | 10/2013 | Matusaitis et al. |
| 8,702,626 B1 | 4/2014 | Kim et al. |
| 9,167,961 B2 | 10/2015 | Makower et al. |
| 9,198,736 B2 | 12/2015 | Kim et al. |
| 9,592,087 B2 | 3/2017 | Brunnett et al. |
| 9,649,125 B2 | 5/2017 | Truckai |
| 10,631,890 B2 | 4/2020 | Palushi et al. |
| 11,103,256 B2 | 8/2021 | Akbarian et al. |
| 2005/0165420 A1 | 7/2005 | Cha |
| 2007/0208252 A1 | 9/2007 | Makower |
| 2008/0077145 A1 | 3/2008 | Boyden et al. |
| 2009/0270888 A1* | 10/2009 | Patel ................. A61B 17/32002 606/159 |
| 2010/0179557 A1* | 7/2010 | Husted ............. A61B 17/32002 600/300 |
| 2011/0060214 A1 | 3/2011 | Makower |
| 2011/0237940 A1* | 9/2011 | Raleigh .............. A61B 1/00177 600/425 |
| 2014/0200444 A1 | 7/2014 | Kim et al. |
| 2014/0364725 A1 | 12/2014 | Makower |
| 2016/0008083 A1 | 1/2016 | Kesten et al. |
| 2016/0151120 A1* | 6/2016 | Kostrzewski .......... A61B 90/50 606/130 |
| 2016/0310042 A1 | 10/2016 | Kesten et al. |
| 2017/0095264 A1 | 4/2017 | Schmitz et al. |
| 2018/0325618 A1* | 11/2018 | Justin .................... A61B 90/37 |
| 2019/0029697 A1 | 1/2019 | Anderson et al. |
| 2022/0409298 A1* | 12/2022 | Haider .................. A61B 34/20 |

OTHER PUBLICATIONS

U.S. Appl. No. 62/555,824, entitled "Apparatus to Secure Field Generating Device to Chair," filed Sep. 8, 2017.

* cited by examiner

FIG. 8

SHAVER WITH BLOOD VESSEL AND NERVE MONITORING FEATURES

PRIORITY

This application is a division of U.S. patent application Ser. No. 15/984,473, entitled "Shaver with Blood Vessel and Nerve Monitoring Features," filed May 21, 2018, and issued as U.S. Pat. No. 11,103,256 on Aug. 31, 2021.

BACKGROUND

Surgical cutting instruments configured for removal of lesions, polyps and fibroids within the nasal cavity are known. Some configurations may include an elongated inner member rotatably coaxially disposed within a tubular outer member. The distal end of the outer member includes an opening, and the distal end of the inner member includes cutting edges. The proximal ends of the two members may be connected to a handle directly or via a detachable hub. The inner member may be hollow and in communication with an aspiration port so that severed tissue, etc. can be aspirated out through the hollow member. The cutting edges can have any various configurations suitable for the particular type of tissue, such as bone tissue, to be done, with the opening configured to cooperate with the specific cutting edge configuration.

To use such surgical cutting instrument to address such tissues, the opening/cutting edge is advanced to the target surgical site, and the opening positioned adjacent the tissue to be removed. The opening may be repositioned to address tissue which could not be accessed with the instrument in the previous position. Surgical cutting instruments with a fixed opening allow surgeons to cut only in the direction of the fixed opening cutting. To access, cut and remove tissue at various locations, surgeons have to reposition the instrument at various angles; or in some instances, change to other instruments having a more appropriately arranged opening.

It may be desirable to access, cut and remove tissue, such as bone tissue, at various locations without having to reposition or change the surgical instrument. While several different surgical instruments and methods of use have been made for tissue removal within the nasal cavity, it is believed that no one prior to the inventors has made or used the invention described in the appended claims.

BRIEF DESCRIPTION OF THE DRAWINGS

While the specification concludes with claims which particularly point out and distinctly claim the invention, it is believed the present invention will be better understood from the following description of certain examples taken in conjunction with the accompanying drawings, in which like reference numerals identify the same elements and in which:

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

It will be appreciated that the terms "proximal" and "distal" are used herein with reference to a clinician gripping a handpiece assembly. Thus, an end effector is distal with respect to the more proximal handpiece assembly. It will be further appreciated that, for convenience and clarity, spatial terms such as "side," "axial," and "longitudinal" also are used herein for reference to relative positions and directions. However, surgical instruments are used in many orientations and positions, and these terms are not intended to be limiting and absolute.

It is further understood that any one or more of the teachings, expressions, versions, examples, etc. described herein may be combined with any one or more of the other teachings, expressions, versions, examples, etc. that are described herein. The following-described teachings, expressions, versions, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

I. Exemplary Surgical Cutting Instrument

Figure 1:
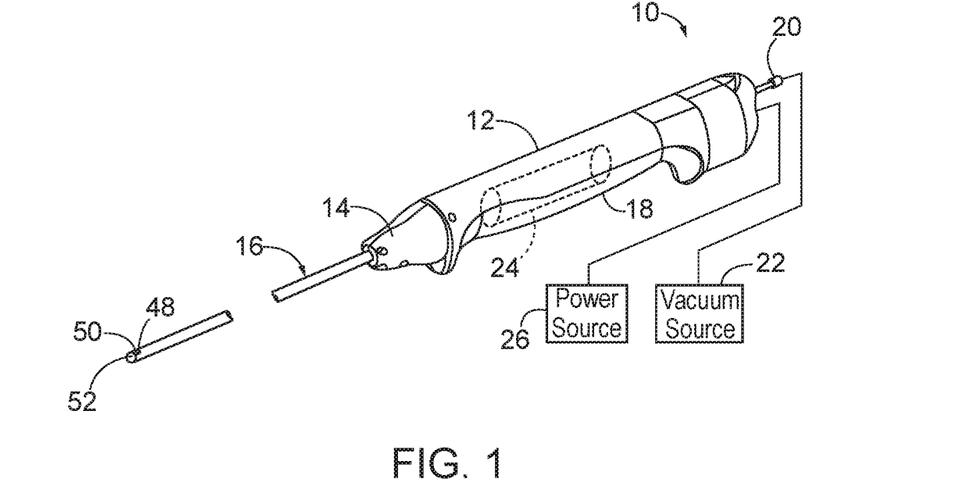
FIG. 1 depicts a perspective view of a first exemplary surgical cutting instrument having a handle assembly and a first shaft assembly.
Figure 2:
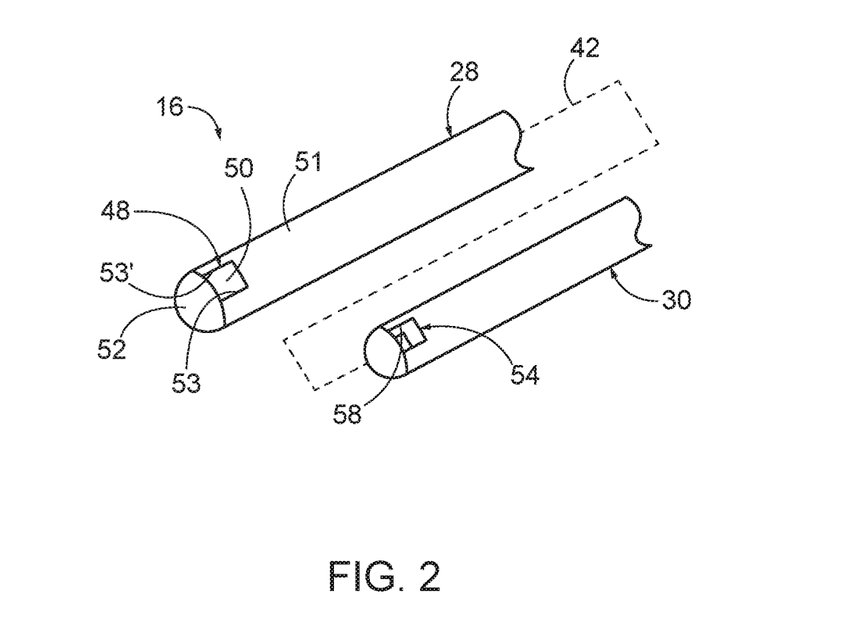
FIG. 2 depicts an exploded perspective fragmentary view of the shaft assembly of FIG. 1 having a shaft and a cutting member.

FIG. 1-2 show a first exemplary surgical cutting instrument (10) that may be used to remove tissue, such as bone tissue, from the nasal cavity, as well as from any other suitable location. Surgical cutting instrument (10) of the present example includes a handle assembly (12), a hub (14), and a first shaft assembly (16) extending distally from handle assembly (12). Handle assembly (12) has a handle (18) which may be of any suitable configuration. Handle (18) may include controls for the operation of surgical cutting instrument (10), or the controls may be located remotely. Surgical cutting instrument (10) further includes a suction port (20) operatively connected to a vacuum source (22) and configured to enable aspiration of tissue, such as a bone tissue, from a surgical site. Rotational motion is delivered by a motorized drive assembly (24) within handle assembly (12) to shaft assembly (16) in the present example, although any suitable rotational or oscillatory motion source may be utilized. For example, such motion source may be housed within handle assembly (12) or may be external and connectable to handle assembly (12). A power source (26) connects to motorized drive assembly (24) to power surgical cutting instrument (10) for use. In addition or alternatively, handle assembly (12) may house a battery (not shown).

Shaft assembly (16) generally includes an outer shaft (28) and an inner cutting member (30) collectively configured to receive and remove tissue from the surgical site. Cutting member (30), which is illustrated as a tube, is disposed within a longitudinally extending lumen (32) of shaft (28). Cutting member (30) is configured to be rotated about a longitudinal axis (42) of shaft assembly (16) at a distal portion. Although shaft assembly (16) is depicted as rigid, all or a portion of shaft assembly (16) may be flexible, with longitudinal axis (42) comprising a series of cross-sectional centers. Cutting member (30) defines a lumen and extends proximally to handle assembly (12) and connects to motorized drive assembly (24), which rotatably drives cutting member (30) relative to shaft (28). In the present example, shaft (28) is formed of polycarbonate and cutting member (30) is formed of stainless steel. Of course, shaft (28) and cutting member (30) may be formed of one or more alternative materials in accordance with the invention described herein. The invention is thus not intended to be unnecessarily limited to manufacture with polycarbonate and stainless steel. While the present example of cutting member (30) is a hollow tube, cutting member (30) is not limited to being tubular and defining its own lumen (32).

Shaft (28) includes a window region (48) having a shaft opening, such as a shaft window opening (50), at distal portion. Distal portion includes a tubular sidewall (51) that distally terminates in a curved end, such as a generally hemispherical end (52). Shaft window opening (50) extends through tubular sidewall (51) of shaft (28) into central lumen (40) and is in fluid communication with the environment surrounding shaft (28). Shaft window opening (50) faces radially outward relative to longitudinal axis (42) such that tissue is configured to be radially received through shaft window opening (50) into central lumen (40) in a radially inward direction. Shaft window opening (50) is surrounded by a relatively dull edge (53).

Cutting member (30) includes a cutting window opening (54) at distal portion of cutting member (30). Cutting window opening (54) is configured to longitudinally align with shaft window opening (50) and includes a cutting edge (58) extending therealong. It is noted that less than the entirety of cutting edge (58) may be configured for cutting tissue against an opposing edge (53) of shaft (28). At least a portion of cutting edge (58) is disposed to move adjacent to and across at least a portion of window region (48) when cutting member (30) is rotated or oscillated about longitudinal axis (42). By way of example, as cutting member (30) moves in a clockwise direction, edge (53) of window region (48) provides an opposing surface to cutting edge (58) whereby tissue may be severed to remove a cut tissue portion therefrom. Cutting edge (58) and edge (53) may have any configuration which suitably cooperates with the other to sever tissue, such as a knife edge, a serrated edge, bipolar, monopolar or harmonic energy modality, or laser activated cutting edge.

The extent of movement and position of cutting edge (58) relative to edge (53) is sufficient to separate tissue, whether by severing, tearing or any other mechanism. For example, cutting edge (58) may cyclically move across at least a portion of window region (48). Further clockwise movement of cutting member (30) will advance cutting edge (58) past edge (53), such as results from oscillation about longitudinal axis (42) or from full rotation about longitudinal axis (42).

With continued reference to FIGS. 1-2, vacuum source (22) generates suction in a proximal direction along longitudinal axis (42) toward suction port (20). Without tissue blocking cutting window opening (54), such suction proximally withdraws a window airflow therethrough along lumen. However, once tissue is respectively introduced into window opening (54), suction effectively draws tissue into window opening (54) for resection while tissue blocks airflow along lumen. Airflow through lumen essentially terminates such that vacuum source (22) accumulates the vacuum within lumen. Such termination of airflow may generally be referred to as a stalled airflow within lumen. Additional details regarding airflow through lumen and aspiration vents for improving such airflow are discussed in alternative examples described in U.S. patent application Ser. No. 15/795,473, entitled "Tissue Shaving Instrument," filed Oct. 27, 2017, issued as U.S. Pat. No. 10,631,890 on Apr. 28, 2020, the disclosure of which is incorporated by reference herein.

Furthermore, surgical cutting instrument (10) may be used in conjunction with an image-guide surgery (IGS) navigation system, medical procedure chair, and displays described alone or in any combination according to the following: U.S. Pat. Pub. No. 2016/0008083, entitled "Guidewire Navigation for Sinuplasty," published Jan. 14, 2016, issued as U.S. Pat. No. 10,463,242 on Nov. 5, 2019; U.S. Patent App. No. 62/555,824, entitled "Apparatus to Secure Field Generating Device to Chair," filed Sep. 8, 2017; U.S. Pat. Pub. No. 2016/0008083, entitled "Guidewire Navigation for Sinuplasty," published Jan. 14, 2016, issued as U.S. Pat. No. 10,463,242 on Nov. 5, 2019; U.S. Pat. Pub. No. 2016/0310042, entitled "System and Method to Map Structures of Nasal Cavity," published Oct. 27, 2016, issued as U.S. Pat. No. 10,362,965 on Jul. 30, 2019; U.S. Pat. No. 8,702,626, entitled "Guidewires for Performing Image Guided Procedures," issued Apr. 22, 2014; U.S. Pat. No. 8,320,711, entitled "Anatomical Modeling from a 3-D Image and a Surface Mapping," issued Nov. 27, 2012; U.S. Pat. No. 8,190,389, entitled "Adapter for Attaching Electromagnetic Image Guidance Components to a Medical Device," issued May 29, 2012; U.S. Pat. No. 8,123,722, entitled "Devices, Systems and Methods for Treating Disorders of the Ear, Nose and Throat," issued Feb. 28, 2012; U.S. Pat. No. 7,720,521, entitled "Methods and Devices for Performing Procedures within the Ear, Nose, Throat and Paranasal Sinuses," issued May 18, 2010; U.S. Pat. Pub. No. 2014/0364725, entitled "Systems and Methods for Performing Image Guided Procedures within the Ear, Nose, Throat and Paranasal Sinuses," published Dec. 11, 2014, now abandoned; U.S. Pat. Pub. No. 2014/0200444, entitled "Guidewires for Performing Image Guided Procedures," published Jul. 17, 2014, now abandoned; U.S. Pat. No. 9,198,736, entitled "Adapter for Attaching Electromagnetic Image Guidance Components to a Medical Device," issued Dec. 1, 2015; U.S. Pat. Pub. No. 2011/0060214, entitled "Systems and Methods for Performing Image Guided Procedures within the Ear, Nose, Throat and Paranasal Sinuses," published Mar. 10, 2011, now abandoned; U.S. Pat. No. 9,167,961, entitled "Methods and Apparatus for Treating Disorders of the Ear Nose and Throat," issued Oct. 27, 2015; and U.S. Pat. Pub. No. 2007/0208252, entitled "Systems and Methods for Performing Image Guided Procedures within the Ear, Nose, Throat and Paranasal Sinuses," published Sep. 6, 2007, now abandoned, the disclosures of each of the these references being incorporated by reference herein.

II. Tissue Monitor Systems for a Surgical Cutting Instrument with a Tissue Sensor While surgical cutting instrument (10) is configured to remove a target tissue as discussed above in greater detail, such surgical cutting instrument (10) may be used by an operator to inadvertently cut a desirable tissue, which would preferably remain intact within the patient. Particularly in instances with small and/or complicated tissue anatomies, the target tissue may be relatively close and, in some instances, even intertwined with the desirable tissue. The operator of surgical cutting instrument (10) may thus require significant skill and time during treatment to carefully remove the target tissue surgical cutting instrument (10) or risk inadvertently cutting or even removing such desirable tissue.

Various surgical cutting instruments (110, 210) discussed below incorporate a tissue monitor system (182, 282) for detecting the desirable tissue while removing the target tissue to thereby reduce the likelihood of inadvertently damaging the desirable tissue during use. Two such surgical cutting instruments (110, 210) and tissue monitor systems (182, 282) in the present examples cut and remove tissue with cutting edge (58) discussed above and a drill (230) discussed below, while detecting nerve tissue and/or blood vessels, but it will be appreciated that any such instruments configured for cutting tissue within the patient may be so used. To this end, any feature or associated use of the various tissue monitor systems (182, 282) may be used alone or in combination with each other. For example, tissue monitor system (182) is configured to detect nerve tissue, whereas, tissue monitor system (282) is configured to detect blood vessels, but such features are readily combinable such that an alternative tissue monitor system may detect both nerve tissue and blood vessels in use. The invention is thus not intended to be unnecessarily limited to the particular examples shown herein. In any case, like numbers provided below indicate like features discussed above in greater detail.

A. Various Surgical Cutting Instruments and Tissue Sensors

Figure 3:
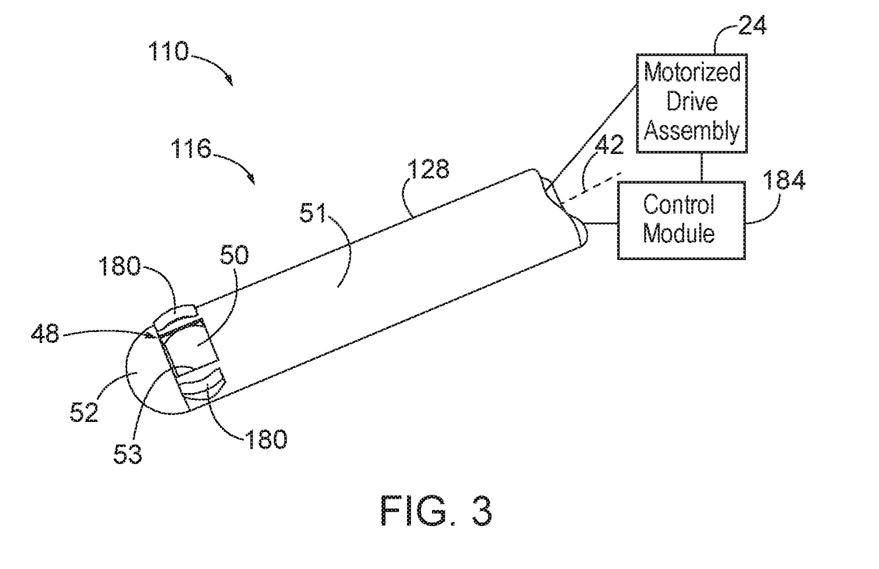
FIG. 3 depicts an enlarged perspective view of a second exemplary surgical cutting instrument having a pair of tissue sensors for a tissue monitor system.

FIG. 3 shows a second exemplary surgical cutting instrument (110) having a second shaft assembly (116) with an outer tube (128) and a pair of tissue sensors (180) for use with a nerve tissue monitor system (182) (see FIG. 5) and/or a vessel tissue monitor system (282) (see FIG. 7) discussed below in greater detail. In this respect, each tissue sensor (180) is more particularly a nerve sensor electrode (180), but may additionally or alternatively be an infrared sensor (280) (see FIG. 4) or an ultrasound sensor. Nerve sensor electrodes (180) are generally configured to detect the desirable tissue by distinguishing the desirable tissue from the target tissue in order to reduce the likelihood of inadvertently damaging the desirable tissue during use while simultaneously removing the target tissue between cutting edge (58) and opposing edge (53).

In the present example, nerve sensor electrodes (180) are fixed to outer tube (128) such that shaft window opening (50) is positioned between the pair of nerve sensor electrodes (180). More particularly, shaft window opening (50) includes longitudinally extending edges (53, 53') that are parallel and angularly offset from each other about longitudinal axis (42). Each nerve sensor electrode (180) is angularly positioned proximate to respective edges (53, 53') about longitudinal axis (42). Nerve sensor electrodes (180) thus collectively straddle shaft window opening (50) about longitudinal axis (42) to increase the likelihood of detecting nerve tissue being introduced into shaft window opening (50) during use.

Each nerve sensor electrode (180) is electrically connected to a control module (184) contained with handle assembly (12) (see FIG. 1). In addition, control module (184) is electrically connected to motorized drive assembly (24), which drives rotation of inner cutting member (30) (see FIG. 2). Based on detected nerve tissue via nerve sensor electrodes (180), control module (184) thereby directs rotation of inner cutting member (30) to either cease driving rotation of inner cutting member (30) or simply prevent rotation regardless of input provided by the operator to inhibit damaging the detected desirable tissue. Alternatively, the operator may receive feedback of the detected tissue such that the operator may selectively direct movement of cutting member (30) as desired.

Figure 4:
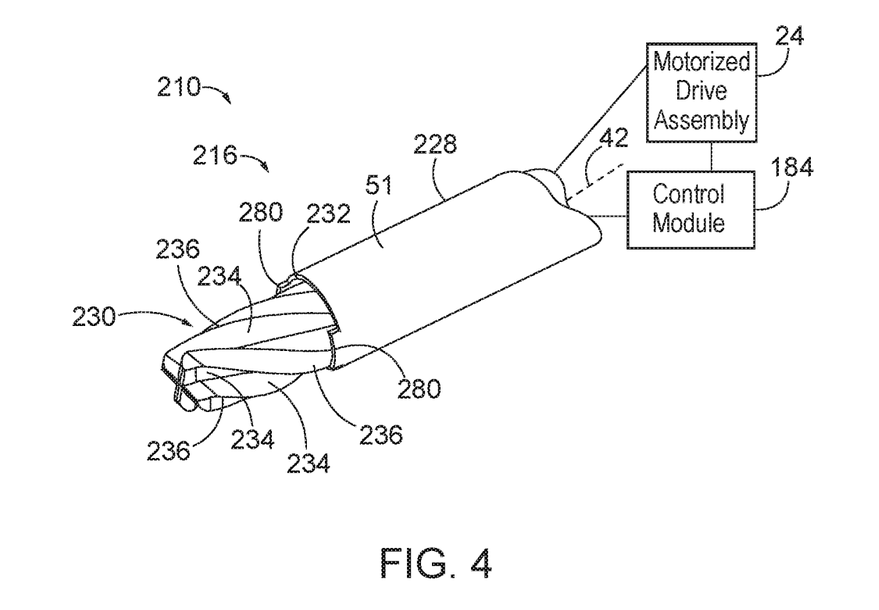
FIG. 4 depicts an enlarged perspective view of a third exemplary surgical cutting instrument having another pair of tissue sensors for a tissue monitor system.

Alternatively, FIG. 4 shows a third exemplary surgical cutting instrument (210) having a third shaft assembly (216) with an outer tube (228) and a pair of tissue sensors (280) for use with nerve tissue monitor system (182) (see FIG. 5) and/or vessel tissue monitor system (282) (see FIG. 7) discussed below in greater detail. In this respect, each tissue sensor (280) is more particularly an infrared sensor (280), but may be an alternative sensor, such as the ultrasound sensor. Infrared sensors (280) are generally configured to detect the desirable tissue by distinguishing the desirable tissue from the target tissue in order to reduce the likelihood of inadvertently damaging the desirable tissue during use while simultaneously removing the target tissue with another cutting member, such as a drill (230).

Outer tube (228) extends to a distal edge (232) surrounding a shaft opening of outer tube (228). Longitudinal axis (42) thus extends coaxially through the shaft opening, which is configured to receive drill (230) therethrough. More particularly, drill (230) has a plurality of flutes (234) spiraling longitudinally therealong with a respective plurality of cutting edges (236). Each cutting edge (236) cuts the target tissue such that drill (230) is configured to bore a hole into the target tissue for removing at least a portion of the target tissue. Drill (230) is connected to motorized drive assembly (24) such that motorized drive assembly (24) is configured to drive rotation of drill (230) relative to outer tube (228) during use.

In the present example, infrared sensors (280) face distally and extend distally from distal edge (232) of outer tube (128) such that the shaft opening is positioned between the pair of infrared sensors (280). More particularly, infrared sensors (280) are positioned on angularly opposed sides of outer tube (228) about longitudinal axis (42). Drill (230) with cutting edges (236) extends distally beyond distal edge (232) and infrared sensors (280) such that cutting edges (236) cut the target tissue while infrared sensors (280) are configured to detect the desirable tissue during use.

Each infrared sensor (280) is electrically connected to control module (184) contained with handle assembly (12) (see FIG. 1). In addition, control module (184) is electrically connected to motorized drive assembly (24). Based on detected blood vessels via infrared sensors (280), control module (184) thereby directs rotation of drill (230) to either cease driving rotation of drill (230) or simply prevent rotation regardless of input provided by the operator to inhibit damaging the detected desirable tissue. Alternatively, the operator may receive feedback of the detected tissue such that the operator may selectively direct movement of drill (230) as desired.

B. Tissue Monitor Systems for Nerve Tissue and Blood Vessels

Figure 5:
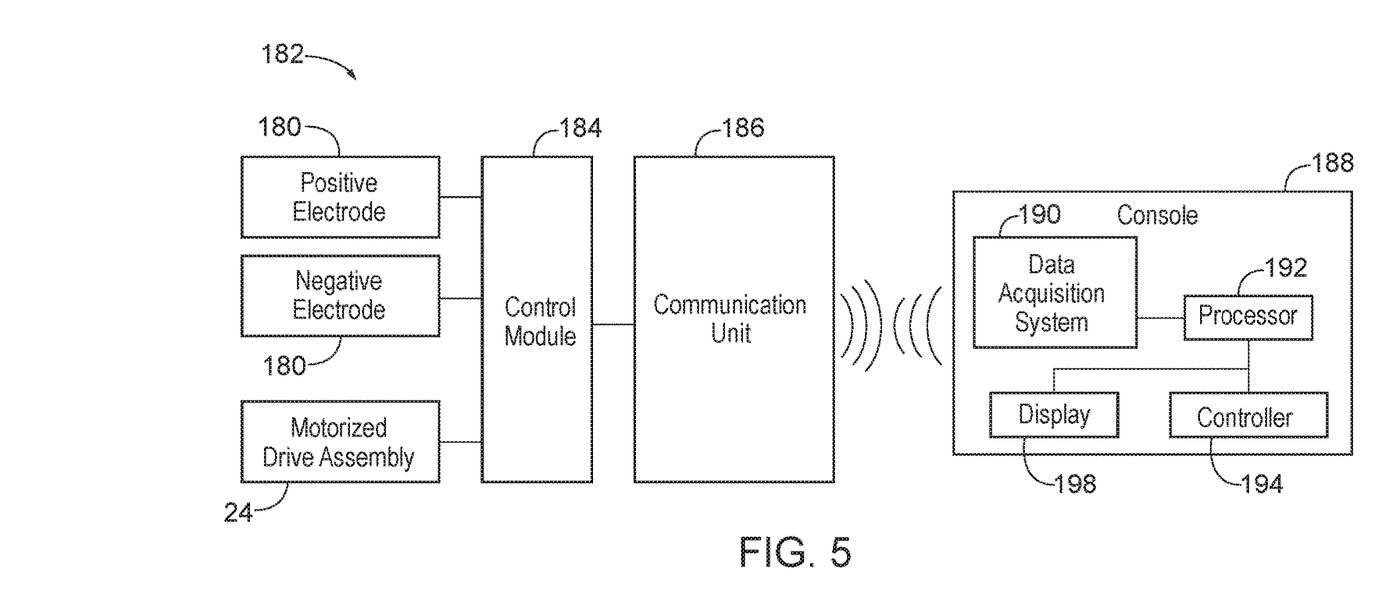
FIG. 5 depicts a diagrammatic view of a nerve tissue monitor system.

FIG. 5 shows nerve tissue monitor system (182) in greater detail including the pair of nerve sensor electrodes (180) and motorized drive assembly (24) connected to control module (184) as discussed briefly above. Control module (184) connects to a communication unit (186) that wirelessly communicates with a console (188). To this end, nerve sensor electrodes (180) are positioned on shaft assembly (116), whereas each of control module (184) and communication unit (186) are contained within handle assembly (12) and configured to exchange data remotely with console (188). In the present example, nerve sensor electrodes (180) continuously measure electrical parameters and communicate those measurements to control module (184) and communication unit (186) to be sent to console (188) for collection and processing for further control.

In the present example, console (188) includes a data acquisition system (190), a processor (192), a controller (194), and a feedback device, such as a display (198). Data acquisition system (190) collects the measurement data provided by nerve sensor electrodes (180), and processor (192) processes the measurement data for visualizing on display (198). In addition, processor (192) and controller (194) analyze the measurement data to determine if nerve tissue is present across nerve sensor electrodes (180). Thereby, processor (192) and controller (194) are configured to detect such nerve tissue.

Controller (194) of the present example is further configured to wirelessly communicate the status of detected nerve tissue back to communication unit (186). In the event that controller (184) detects nerve tissue, controller (194) directs control module (184) to deactivate motorized drive assembly (24) in order to cease driving cutting member (30). Thereby, controller (194) actively inhibits the operator from inadvertently cutting the nerve tissue.

Figure 6A:
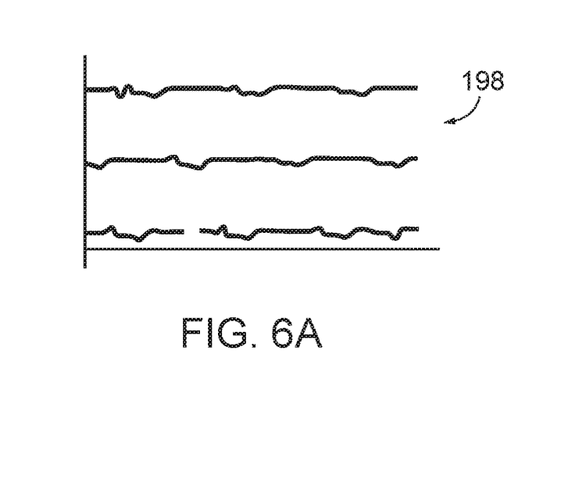
FIG. 6A depicts a schematic view of a display of the nerve tissue monitor system of FIG. 5 in use without the presence of nerve tissue being detected.
Figure 6B:
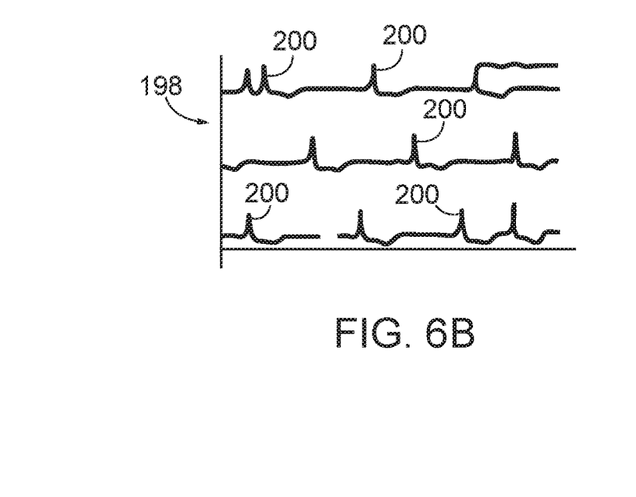
FIG. 6B depicts the schematic view of the display similar to FIG. 6A, but showing the nerve tissue monitor system in use with the presence of nerves being detected.

Additionally or alternatively, controller (194) may be configured to provide passive feedback to the operator via display (198). For example, controller (194) directs display to visually generate images of the measurement data for viewing by the operator as shown in FIGS. 6A-6B. FIG. 6A shows electrical measurements being approximately continuous without the detection of nerve tissue. In contrast, FIG. 6B shows a plurality of electrical measurement spikes (200) indicative of the presence of nerve tissue. In the case of controller (194) actively ceasing movement of cutting member (30), the operator may override controller (194) to continue driving cutting member (30) based on the passive feedback visualized on display (198). In another example, control (194) may entirely prevent the operator from selectively driving cutting member (30) while detecting nerve tissue. In the case of receiving the passive feedback via display (198), the operator may either continue to proceed with cutting, adjust the position of cutting member (30) to avoid the nerve tissue, and/or selectively cease driving cutting member (30) for further inspection or adjustment.

While the feedback discussed above is visual, alternative feedback may include audible feedback by an audible generator (not shown) or tactile feedback by a tactile feedback generator (not shown). The particular feedback provided herein is thus not intended to unnecessarily limit the invention. Furthermore, various aspects of console (188) may be contained within shaft assembly (116) and/or handle assembly (12) in another example such that wireless communication is reduced or simply eliminated, and one or more components combined as desired. For example, functionality of control module (184) and controller (194) may be combined or separated as desired. The terms "control module" and "controller" are interchangeable and not intended to unnecessarily limit the invention described herein. Furthermore, it will be appreciated that such tissue monitor system (182) may be similarly configured for detecting target tissue with one or more ultrasound sensors.

Figure 7:
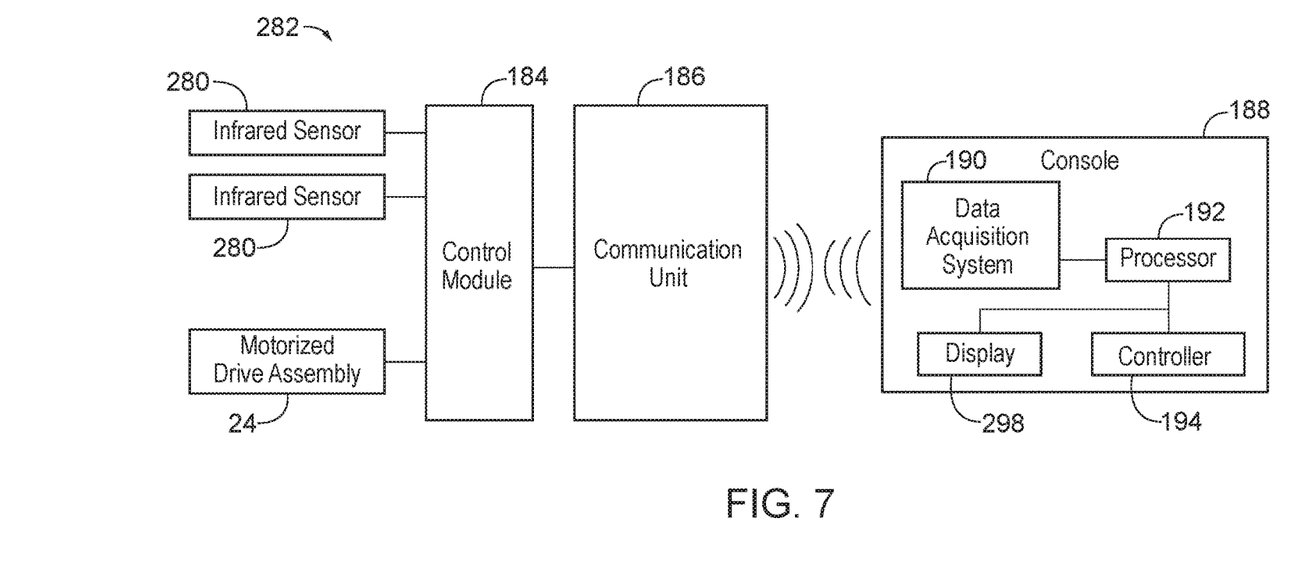
FIG. 7 depicts a diagrammatic view of a vessel tissue monitor system.
Figure 8:
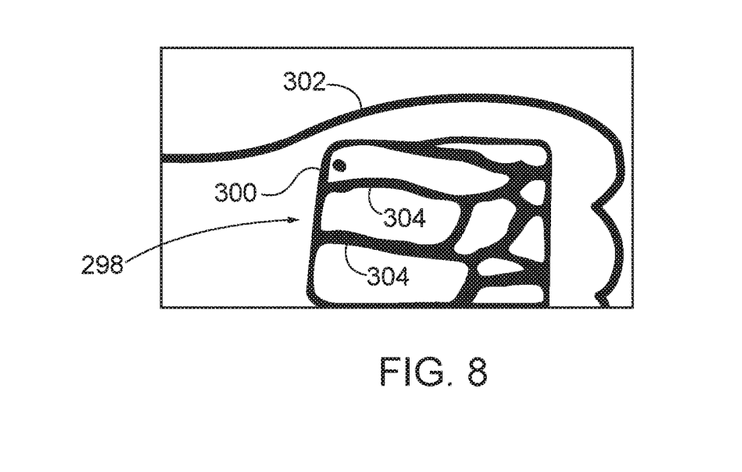
FIG. 8 depicts a schematic view of a display of the vessel tissue monitor system of FIG. 7 in use with the presence of blood vessels being detected.

FIGS. 7-8 show vessel tissue monitor system (282) in greater detail including the pair of infrared sensors (280) and motorized drive assembly (24) connected to control module (184) as discussed briefly above. Similar to nerve tissue monitor system (182) (see FIG. 5), vessel tissue monitor system (282) also includes control module (184), communication unit (186) contained within handle assembly (12) as well as data acquisition system (190), processor (192), and controller (194) contained within a console (288). In this respect vessel tissue monitor system (282) is configured to function similarly to nerve tissue monitor system (182) (see FIG. 5) such that like numbers indicate like features discussed above.

Console (288) differs from console (188) (see FIG. 5) with the inclusion of a projection display (298) configured to display a projected image (300) onto an anatomy, such as a hand (302), of the patient. In the present example, infrared sensors (280) detect blood vessels, which are processed by processor (192) and directed by controller (194) to be projected by projection display (298) onto the hand (302). Projection display (298) visualizes blood vessels as a plurality of imaged blood vessels (304) projected and mapped directly on the hand (302). The operator may thus selectively direct movement of shaft assembly (216) while cutting the target tissue to avoid the blood vessels (304) by using the mapped imaged blood vessels (304) as a guide. Again, it will be appreciated that such tissue monitor system (282) may be similarly configured for detecting target tissue with one or more ultrasound sensors.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A surgical instrument, comprising: (a) a shaft extending along a longitudinal axis and including: (i) a shaft lumen extending along the longitudinal axis, and (ii) a shaft opening in fluid communication with an environment and the shaft lumen; (b) a cutting member disposed within the shaft lumen and configured to cyclically move from a first position to a second position relative to the shaft, wherein the cutting member is configured to cut a tissue portion of a first tissue for removal therefrom; and (c) a tissue monitor system associated with at least one of the shaft or the cutting member, wherein the tissue monitor system is configured to detect a second tissue distinct from the first tissue for selectively cutting and removing the first tissue relative to the second tissue.

Example 2

The surgical instrument of Example 1, wherein the tissue monitor system further includes a first tissue sensor configured to detect the second tissue.

Example 3

The surgical instrument of Example 2, wherein the tissue monitor system further includes a second tissue sensor configured to further detect the second tissue.

Example 4

The surgical instrument of Example 3, wherein the first and second tissue sensors are positioned on the shaft.

Example 5

The surgical instrument of any one or more of Examples 3 through 4, further comprising a motorized drive assembly operatively connected to the cutting member and configured to drive the cutting member to cyclically move, wherein the tissue monitor system further includes a controller operatively connected to the first and second tissue sensors and the motorized drive assembly, wherein the controller is configured to cease driving the cutting member when at least one of the first or second tissue sensors detect the second tissue.

Example 6

The surgical instrument of Example 5, wherein the controller is configured to cease driving the cutting member when each of the first and second tissue sensors detect the second tissue.

Example 7

The surgical instrument of any one or more of Examples 2 through 6, further comprising a motorized drive assembly operatively connected to the cutting member and configured to drive the cutting member to cyclically move, wherein the tissue monitor system further includes a controller operatively connected to the first sensor and the motorized drive assembly, wherein the controller is configured to cease driving the cutting member when the first tissue sensor detects the second tissue.

Example 8

The surgical instrument of Example 7, wherein the first tissue sensor is positioned on the shaft.

Example 9

The surgical instrument of claim 2, wherein the first tissue sensor is a first nerve sensor electrode configured to detect the second tissue in the form of a nerve tissue.

Example 10

The surgical instrument of any one or more of Examples 2 through 9, wherein the first tissue sensor is a first infrared sensor configured to detect the second tissue in the form of a blood vessel.

Example 11

The surgical instrument of any one or more of Examples 1 through 10, wherein the tissue monitor system further includes a feedback device configured to indicate detection of the second tissue to an operator.

Example 12

The surgical instrument of Example 11, wherein the feedback device includes a display configured to visually indicate detection of the second tissue to the operator.

Example 13

The surgical instrument of any one or more of Examples 1 through 12, further comprising a suction lumen extending along the longitudinal axis in fluid communication with the shaft opening and configured to connect to a vacuum source.

Example 14

The surgical instrument of any one or more of Examples 1 through 13, wherein the shaft opening is a shaft window opening configured to receive the first tissue therein from the environment, and wherein the cutting member further includes: (i) a cutting window opening in fluid communication with the shaft window opening in the first position and configured to receive the first tissue therein, (ii) a cutting edge at least partially surrounding the cutting window opening and configured to be cyclically moved within the shaft lumen adjacent to the shaft edge for cutting the tissue portion from the first tissue between the cutting edge and the shaft edge, and (iii) a suction lumen extending along the longitudinal axis in fluid communication with the cutting window opening and configured to connect to a vacuum source, wherein the suction lumen is in fluid communication with the cutting window opening and the shaft window opening in the first position.

Example 15

The surgical instrument of any one or more of Examples 1 through 14, wherein the shaft opening is coaxially aligned with the longitudinal axis, wherein the cutting member further includes: (i) a drill projecting distally from the shaft opening, and (ii) a plurality of cutting edges extending along the drill configured to cut the tissue portion from the first tissue.

Example 16

A surgical instrument, comprising: (a) a shaft extending along a longitudinal axis and including: (i) a shaft lumen extending along the longitudinal axis, and (ii) a shaft opening in fluid communication with an environment and the shaft lumen; (b) a cutting member disposed within the shaft lumen and configured to cyclically move from a first position to a second position relative to the shaft, wherein the cutting member is configured to cut a tissue portion of a first tissue for removal therefrom; (c) a motorized drive assembly operatively connected to the cutting member and configured to drive the cutting member to cyclically move; and (d) a tissue monitor system associated with at least one of the shaft or the cutting member, wherein the tissue monitor system is configured to detect a second tissue distinct from the first tissue for selectively cutting and removing the first tissue relative to the second tissue, wherein the tissue monitor system includes: (i) a first tissue sensor positioned on the shaft, (ii) a second tissue sensor positioned on the shaft, and (iii) a controller operatively connected to the first and second tissue sensors and the motorized drive assembly, wherein the controller is configured to cease driving the cutting member when at least one of the first or second tissue sensors detect the second tissue.

Example 17

The surgical instrument of Example 16, wherein the controller is configured to cease driving the cutting member when each of the first and second tissue sensors detect the second tissue.

Example 18

The surgical instrument of any one or more of Examples 16 through 17, wherein the shaft opening is a shaft window opening positioned angularly between the first and second tissue sensors about the longitudinal axis and configured to receive the first tissue therein from the environment, and wherein the cutting member further includes: (i) a cutting window opening in fluid communication with the shaft window opening in the first position and configured to receive the first tissue therein, (ii) a cutting edge at least partially surrounding the cutting window opening and configured to be cyclically moved within the shaft lumen adjacent to the shaft edge for cutting the tissue portion from the first tissue between the cutting edge and the shaft edge, and (iii) a suction lumen extending along the longitudinal axis in fluid communication with the cutting window opening and configured to connect to a vacuum source, wherein the suction lumen is in fluid communication with the cutting window opening and the shaft window opening in the first position.

Example 19

The surgical instrument of any one or more of Examples 16 through 18, wherein the shaft has a distal edge and the shaft opening is coaxially aligned with the longitudinal axis surrounded by the distal edge, wherein the first and second tissue sensors are positioned on the distal edge, and wherein the cutting member further includes: (i) a drill projecting distally from the distal edge and the shaft opening, and (ii) a plurality of cutting edges extending along the drill configured to cut the tissue portion from the first tissue.

Example 20

A method of cutting a first tissue proximate to a second tissue with a surgical instrument including a shaft, a cutting member, and a tissue monitor system, wherein the shaft extends along a longitudinal axis and includes a shaft lumen extending along the longitudinal axis and a shaft opening in fluid communication with an environment and the shaft lumen, wherein the cutting member is disposed within the shaft lumen and configured to cyclically move from a first position to a second position relative to the shaft, wherein the cutting member is configured to cut a tissue portion of the first tissue for removal therefrom, wherein the tissue monitor system is associated with at least one of the shaft or the cutting member, wherein the tissue monitor system is configured to detect the second tissue distinct from the first tissue, the method comprising: (a) cutting the tissue portion from the first tissue with the cutting member; (b) detecting the second tissue with the tissue monitor system while cutting the tissue portion from the first tissue; and (c) ceasing movement of the cutting member after detecting the second tissue to thereby inhibit cutting the second tissue.

IV. Miscellaneous

It should be understood that any of the examples described herein may include various other features in addition to or in lieu of those described above. By way of example only, any of the examples described herein may also include one or more of the various features disclosed in any of the various references that are incorporated by reference herein.

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices disclosed herein can be designed to be disposed of after a single use, or they can be designed to be used multiple times. Versions may, in either or both cases, be reconditioned for reuse after at least one use.

Reconditioning may include any combination of the steps of disassembly of the device, followed by cleaning or replacement of particular pieces, and subsequent reassembly. In particular, versions of the device may be disassembled, and any number of the particular pieces or parts of the device may be selectively replaced or removed in any combination. Upon cleaning and/or replacement of particular parts, versions of the device may be reassembled for subsequent use either at a reconditioning facility, or by a surgical team immediately prior to a surgical procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be processed before surgery. First, a new or used instrument may be obtained and if necessary cleaned. The instrument may then be sterilized. In one sterilization technique, the instrument is placed in a closed and sealed container, such as a plastic or TYVEK bag. The container and instrument may then be placed in a field of radiation that can penetrate the container, such as gamma radiation, x-rays, or high-energy electrons. The radiation may kill bacteria on the instrument and in the container. The sterilized instrument may then be stored in the sterile container. The sealed container may keep the instrument sterile until it is opened in a surgical facility. A device may also be sterilized using any other technique known in the art, including but not limited to beta or gamma radiation, ethylene oxide, or steam.

Having shown and described various versions of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art. For instance, the examples, versions, geometrics, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A method of cutting a first tissue proximate to a second tissue with a surgical instrument including a shaft, a cutting member, and a tissue monitor system, the shaft extending along a longitudinal axis and including a cylindrical body having a distal edge and a shaft lumen extending along the longitudinal axis and a shaft opening in fluid communication with an environment and the shaft lumen, the cutting member being disposed within the shaft lumen and configured to cyclically move from a first position to a second position relative to the shaft, the cutting member being configured to cut a tissue portion of the first tissue for removal therefrom, the tissue monitor system being associated with at least one of the shaft or the cutting member, the tissue monitor system being configured to detect the second tissue distinct from the first tissue, the method comprising:
    (a) cutting the tissue portion from the first tissue with the cutting member;
    (b) detecting at the distal edge the second tissue with the tissue monitor system while cutting the tissue portion from the first tissue; and
    (c) ceasing movement of the cutting member after detecting the second tissue to thereby inhibit cutting the second tissue.

2. The method of claim 1, the tissue monitor system including a first tissue sensor.

3. The method of claim 2, the first tissue sensor including an ultrasound sensor, the method further comprising:
    detecting the second tissue using the ultrasound sensor, wherein the second tissue being in the form of a blood vessel.

4. The method of claim 2, the first tissue sensor including an infrared sensor, the method further comprising:
    detecting the second tissue using the infrared sensor, the second tissue being in the form of a blood vessel.

5. The method of claim 2, the first tissue sensor being elongate and extending along a majority of a length of the shaft opening.

6. The method of claim 1, further comprising:
    (a) coupling a vacuum source with the shaft lumen; and
    (b) activating the vacuum source to create a vacuum suction within the shaft lumen.

7. The method of claim 6, further comprising:
    extracting the cut tissue portion from the shaft lumen via the vacuum suction.

8. The method of claim 1, the tissue monitor system including a second tissue sensor.

9. The method of claim 1, the tissue monitor system further including a controller operatively connected to the tissue monitor system and a motorized drive assembly, the motorized drive assembly being configured to cyclically move the cutting member within the shaft lumen, the method further including:
    communicating, via the tissue monitor system, a tissue detection signal to the controller indicative of the detection of the second tissue.

10. The method of claim 9, further comprising:
    in response to the controller receiving the tissue detection signal, wirelessly communicating, via a communication unit, the tissue detection signal to a processor for data processing.

11. The method of claim 9, further comprising:
    in response to the controller receiving the tissue detection signal, communicating, via the controller, a drive stop signal to the motorized drive assembly to cease driving the cutting member.

12. The method of claim 1, the tissue monitor system including a feedback device, the method further comprising:
    indicating the detection of the second tissue to an operator.

13. The method of claim 12, the feedback device including a display, the method further comprising:
    visually indicating the detection of the second tissue to the operator via the display.

14. The method of claim 12, the feedback device including a projector, the method further comprising:
    projecting the detection of the second tissue onto a human anatomy via the projector.

15. The method of claim 1, the cutting member including a drill having a plurality of cutting edges, the method further comprising:
    projecting the drill distally from the shaft opening to cut the tissue portion from the first tissue.

16. A method of cutting a first tissue proximate to a second tissue with a surgical instrument including a shaft, a cutting member, and a tissue monitor system, the shaft extending along a longitudinal axis and including a shaft lumen extending along the longitudinal axis and a shaft opening in fluid communication with an environment and the shaft lumen, the shaft lumen being coupled with a vacuum source, the cutting member being disposed within the shaft lumen and configured to cyclically move from a first position to a second position relative to the shaft, the cutting member being configured to cut a tissue portion of the first tissue for removal therefrom, the tissue monitor system being associated with at least one of the shaft or the cutting member, the tissue monitor system being configured to detect the second tissue distinct from the first tissue, the method comprising:
- (a) activating the vacuum source to create a vacuum suction within the shaft lumen;
- (b) aspirating the tissue portion of the first tissue into the shaft lumen;
- (c) activating the cutting member so as to begin cyclical movement of the cutting member;
- (d) cutting the tissue portion of the first tissue once aspirated inside the shaft lumen;
- (e) detecting the second tissue with the tissue monitor system; and
- (f) ceasing movement of the cutting member in response to detecting the second tissue to thereby inhibit cutting the second tissue.

17. The method of claim 16, the tissue monitor system including an electrode, the method further comprising:
   detecting the second tissue using the electrode, the second tissue being in the form of a nerve tissue.

18. The method of claim 16, the tissue monitor system including an infrared sensor, the method further comprising:
   detecting the second tissue using the infrared sensor, the second tissue being in the form of a blood vessel.

19. The method of claim 16, the tissue monitor system including a feedback device, the method further comprising:
   indicating the detection of the second tissue to an operator.

20. A method of cutting a first tissue proximate to a second tissue with a surgical instrument including a shaft, a cutting member, and a tissue monitor system, the shaft extending along a longitudinal axis and including a shaft lumen extending along the longitudinal axis and a shaft opening in fluid communication with an environment and the shaft lumen, the shaft lumen being coupled with a vacuum source, the cutting member including a distal most tip and being disposed within the shaft lumen and configured to cyclically move from a first position to a second position relative to the shaft, the cutting member being configured to cut a bone portion of the first tissue for removal therefrom, the tissue monitor system being associated with at least one of the shaft or the cutting member, the tissue monitor system being configured to detect the second tissue distinct from the first tissue, the method comprising:
- (a) activating the cutting member so as to begin cyclical movement of the distal most tip of the cutting member to cut the bone portion of the first tissue;
- (b) detecting the second tissue with the tissue monitor system, the second tissue including at least one of a nerve tissue or a blood vessel;
- (c) indicating the detection of the second tissue to an operator; and
- (d) ceasing movement of the cutting member after detecting the second tissue to thereby inhibit cutting the second tissue.

* * * * *